United States Patent
Ueno et al.

(10) Patent No.: US 12,042,605 B2
(45) Date of Patent: Jul. 23, 2024

(54) INSOMNIA TREATMENT ASSISTANCE DEVICE, INSOMNIA TREATMENT ASSISTANCE SYSTEM, AND INSOMNIA TREATMENT ASSISTANCE PROGRAM

(71) Applicant: SUSMED, Inc., Tokyo (JP)

(72) Inventors: Taro Ueno, Tokyo (JP); Daisuke Ichikawa, Tokyo (JP)

(73) Assignee: SUSMED, INC., Tokyo (JP)

( * ) Notice: Subject to any disclaimer, the term of this patent is extended or adjusted under 35 U.S.C. 154(b) by 0 days.

(21) Appl. No.: 18/547,426

(22) PCT Filed: Mar. 9, 2021

(86) PCT No.: PCT/JP2021/009162
§ 371 (c)(1),
(2) Date: Aug. 22, 2023

(87) PCT Pub. No.: WO2022/190188
PCT Pub. Date: Sep. 15, 2022

(65) Prior Publication Data
US 2024/0033464 A1    Feb. 1, 2024

(51) Int. Cl.
*A61M 21/00* (2006.01)
*A61B 5/00* (2006.01)
*G16H 20/00* (2018.01)

(52) U.S. Cl.
CPC ........... *A61M 21/00* (2013.01); *A61B 5/4812* (2013.01); *A61B 5/4815* (2013.01); *G16H 20/00* (2018.01); *A61B 5/4836* (2013.01)

(58) Field of Classification Search
CPC .... A61M 21/00; A61B 5/4812; A61B 5/4815; A61B 5/4836; G16H 20/00
See application file for complete search history.

(56) References Cited

U.S. PATENT DOCUMENTS 8,979,730 B2    3/2015    Naujokat et al.
10,772,555 B2    9/2020    Ueno
(Continued)

FOREIGN PATENT DOCUMENTS

EP    3513728 A1    7/2019
JP    2012528655 A    11/2012
(Continued)

OTHER PUBLICATIONS

International Search Report and Written Opinion issued Apr. 27, 2021 for corresponding PCT Application No. PCT/JP2021/009162.
(Continued)

*Primary Examiner* — Ryan W Sherwin
(74) *Attorney, Agent, or Firm* — POLSINELLI PC

(57) ABSTRACT

A bedtime setting unit 13 setting a target bedtime, on the basis of a sleep efficiency of a user, and a compliance status index value calculation unit 14 calculating a compliance status index value representing a compliance status with the set target bedtime are provided, and in a case where the sleep efficiency is less than a first predetermined value and the compliance status index value is a threshold value or more, a time later than the previous set bedtime is set as the next bedtime, in a case where the sleep efficiency is less than the first predetermined value and the compliance status index value is less than the threshold value, a time identical to the previous set bedtime is set as the next bedtime such that even in a state where it is necessary to set the bedtime to be later than the previous set bedtime since the sleep efficiency is less than the first predetermined value, a time identical to the previous set bedtime is set as the next bedtime in a case where the compliance status index value is less than the threshold value, and thus, a bedtime that applies a large burden on a user without an excellent compliance status with the bedtime is not set.

12 Claims, 3 Drawing Sheets

(56) References Cited

U.S. PATENT DOCUMENTS

| | | | |
|---|---|---|---|
| 10,842,968 B1* | 11/2020 | Kahn | G06F 16/9537 |
| 11,004,551 B2* | 5/2021 | Hashizaki | G06N 7/01 |
| 11,478,187 B2* | 10/2022 | Kinnunen | A61B 5/4815 |
| 2017/0049384 A1* | 2/2017 | Yamamoto | G09B 5/02 |
| 2017/0352287 A1* | 12/2017 | Arnold | A61B 5/743 |
| 2018/0303412 A1* | 10/2018 | Moore | G16H 50/20 |
| 2020/0294651 A1* | 9/2020 | Akitomi | G16H 50/20 |
| 2023/0157631 A1* | 5/2023 | Sletten | A61B 5/4815 |
| | | | 600/301 |

FOREIGN PATENT DOCUMENTS

| | | |
|---|---|---|
| JP | 6245781 B1 | 12/2017 |
| JP | 2020054839 A | 4/2020 |
| WO | 2013121662 A1 | 8/2013 |
| WO | 2018069968 A1 | 4/2018 |
| WO | 2018100664 A1 | 6/2018 |

OTHER PUBLICATIONS

Supplementary European Search Report issued on Mar. 18, 2024 for counterpart European Application No. 21 93 0045.6.

Kuhn, Eric et al.: "CBT-I Coach: A Description and Clinician Perceptions of a Mobile App for Cognitive Behavioral Therapy for Insomnia", Journal of Clinical Sleep Medicine [Online] vol. 12, No. 04, Apr. 15, 2016, pp. 597-606, XP093139390.

Lack, Leon C.: "Insomnia Management Kit—Bedtime Restriction Therapy Brochure", Sep. 1, 2017, pp. 1-2 XP093138048.

Spielman, Arthur J. et al.: "Sleep Restriction Therapy" In: "Behavioral Treatments for Sleep Disorders", Jan. 1, 2011, pp. 9-19 XP093138075.

Lichstein, Kenneth L. et al.: "Sleep Compression" In: "Behavioral Treatments for Sleep Disorders", Jan. 1, 2011, pp. 55-59 XP093139480.

Matthews, Ellyn E. et al.: "Adherence to cognitive behavioral therapy for insomnia: A systematic review", Sleep Medicine Reviews, [Online] vol. 17, No. 6, Dec. 1, 2014, pp. 453-464 XP093139483.

* cited by examiner

INSOMNIA TREATMENT ASSISTANCE DEVICE, INSOMNIA TREATMENT ASSISTANCE SYSTEM, AND INSOMNIA TREATMENT ASSISTANCE PROGRAM

CROSS REFERENCE TO RELATED APPLICATIONS

This application is a National Phase filing under 35 U.S.C. § 371 of PCT/JP2021/009162, filed on Mar. 9, 2021; the entire contents of which application is hereby incorporated by reference.

TECHNICAL FIELD

The present invention relates to an insomnia treatment assistance device, an insomnia treatment assistance system, and an insomnia treatment assistance program for assisting a treatment for insomnia.

BACKGROUND ART

Recently, many people suffer from insomnia. The insomnia indicates symptoms such as "insomnia with difficulty in sleep onset" such as having trouble falling asleep, "insomnia with wake after sleep onset" such as being disable to maintain sleep, and "insomnia with premature arousal" such as waking up early in the morning. In a case where such symptoms continue, it is not possible to sleep well, which causes daytime sleepiness, distraction, tiredness, and various deconditioning states.

In the related art, a system for assisting improvement in the quality of the sleep of a user is known (for example, refer to PTLs 1 and 2). In the system described in PTL 1, a sleep efficiency is calculated on the basis of information indicating a bedtime, a fall-asleep time, a wakening time, and a get-up time, which is input by the user to a treatment application, and in a case where the sleep efficiency is less than 80%, a time that is 15 minutes later than the previous set bedtime is set as the next bedtime, and in a case where the sleep efficiency is 85% or more, a time that is 15 minutes earlier than the previous set bedtime is set as the next bedtime. Then, a time that is a predetermined time before the bedtime is set to an implementation time of a sleepiness test, and at the implementation time of the sleepiness test, a demand message for accelerating the implementation of the sleepiness test is presented to the user.

In the system described in PTL 2, individual advice on the user is generated on the basis of a sleep pattern of the user, a change in the sleep pattern, writing a diary, and an individual profile. For example, a bedtime alarm occurs such that the user goes to bed at a statistically suitable time.

SUMMARY OF INVENTION

Technical Problem

As described in PTL 1, setting the bedtime to the time 15 minutes later than the previous set bedtime in a case where the sleep efficiency is less than 80% is to increase the sleep efficiency by reducing the time spent in bed and to gradually improve the quality of the sleep of the user by repeating the above every day. However, delaying the bedtime to reduce the time in bed often applies a psychological burden on people who feel that they do not sleep well, and in a case where a sleep schedule is excessively restricted, there is a concern that compliance decreases.

Note that, PTL 2 discloses entering an examination period for several days in a case where the user does not follow the advice, whereas implementing a compensation policy in a case where the user complies with the advice. However, entering the examination period for several days in a case where the user does not follow the advice is disclosed, but it is also described that the same countermeasure as before is started again by the advice, and thus, what to do during the examination period is not clear.

The invention has been made to solve the problems described above, and an object thereof is to suppress a decrease in the compliance with a set bedtime in a system for assisting improvement in the quality of the sleep of a user by adjusting the bedtime on the basis of a sleep efficiency.

Solution to Problem

In order to attain the object described above, in the invention, a target bedtime is set on the basis of a sleep efficiency calculated on the basis of information indicating a bedtime, a fall-asleep time, a wakening time, and a get-up time of a user and is notified to the user, and a compliance status index value representing a status of whether the user complies with the set target bedtime within a predetermined period is calculated. In particular, in the invention, in the setting of the target bedtime, when the sleep efficiency is less than a first predetermined value and the compliance status index value is a threshold value or more, a time later than the previous set bedtime is set as the next bedtime, when the sleep efficiency is less than the first predetermined value and the compliance status index value is less than the threshold value, a time identical to the previous set bedtime is set as the next bedtime, and when the sleep efficiency is the first predetermined value or more, a time earlier than the previous set bedtime is set as the next bedtime.

Advantageous Effects of Invention

According to the invention configured as described above, even in a state where it is necessary to set the target bedtime to be later than the previous set bedtime in order to reduce the time in bed since the sleep efficiency of the user is less than the first predetermined value, the time identical to the previous set bedtime is set as the next bedtime when the compliance status index value in the predetermined period is less than the threshold value, and thus, the setting of a bedtime that applies a large burden on a user without an excellent compliance status with the bedtime is avoided. Accordingly, it is possible to suppress a decrease in the compliance with the set bedtime.

DESCRIPTION OF EMBODIMENTS

Figure 1:
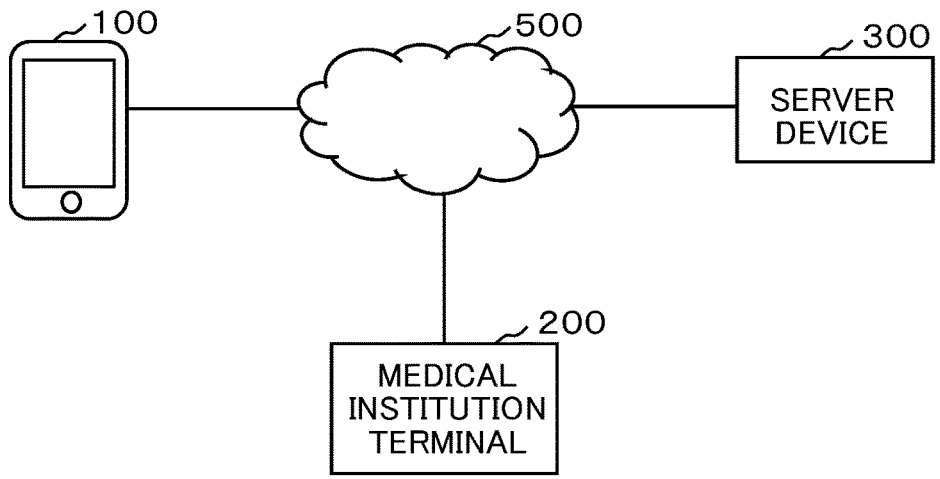
FIG. 1 is a diagram illustrating an overall configuration example of an insomnia treatment assistance system according to this embodiment.

Hereinafter, one embodiment of the invention will be described on the basis of the drawings. FIG. 1 is a diagram illustrating the overall configuration example of an insomnia treatment assistance system according to this embodiment. As illustrated in FIG. 1, the insomnia treatment assistance system according to this embodiment includes a user terminal 100 used by a user, a medical institution terminal 200 used in a medical institution, and a server device 300 connected from the user terminal 100 and the medical institution terminal 200.

The user terminal 100, for example, includes a personal computer, a tablet, a smart phone, and the like. Similarly, the medical institution terminal 200, for example, also includes a personal computer, a tablet, a smart phone, and the like. The user terminal 100 and the server device 300, and the medical institution terminal 200 and the server device 300 are connected through the internet or a communication network 500 such as a mobile phone network.

Figure 2:
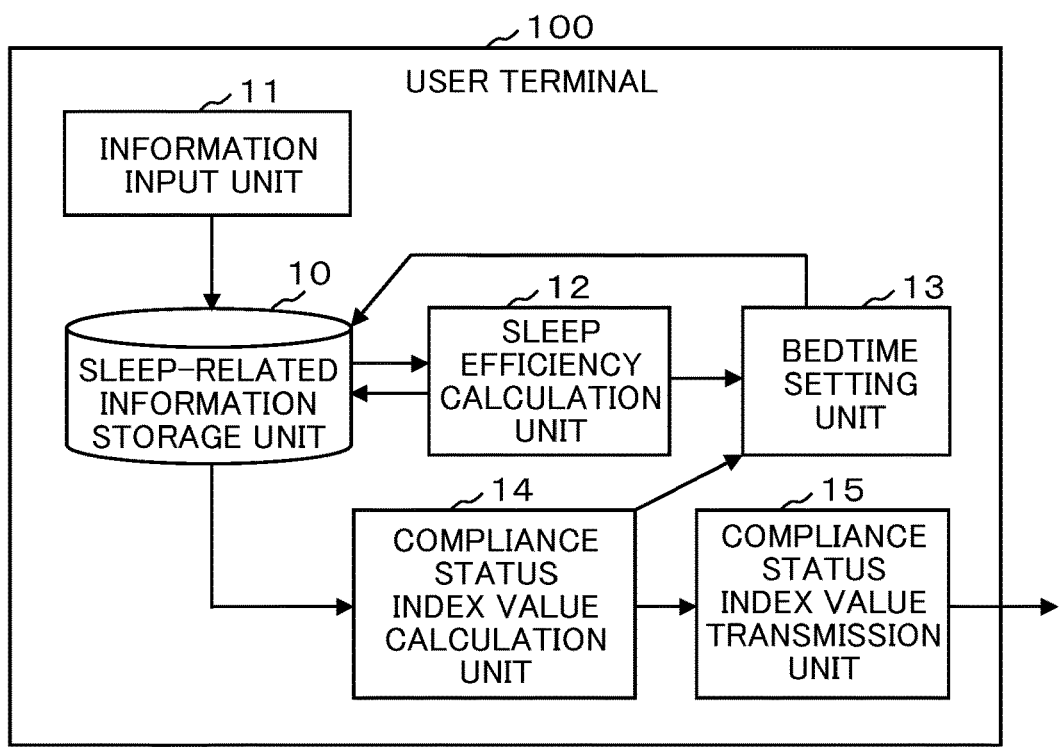
FIG. 2 is a block diagram illustrating a functional configuration example of a user terminal according to this embodiment.

FIG. 2 is a block diagram illustrating a functional configuration example of the user terminal 100 according to this embodiment. As illustrated in FIG. 2, the user terminal 100 of this embodiment includes an information input unit 11, a sleep efficiency calculation unit 12, a bedtime setting unit 13, a compliance status index value calculation unit 14, and a compliance status index value transmission unit 15, as a functional configuration. In addition, the user terminal 100 of this embodiment includes a sleep-related information storage unit 10, as a storage medium. Each of the function blocks 11 to 15 described above configures an insomnia treatment assistance device.

Each of the function blocks 11 to 15 described above can be configured by any of hardware, a digital signal processor (DSP), and software. For example, in a case where the function block is configured by software, each of the function blocks 11 to 15 described above actually includes CPU, RAM, ROM, and the like of a mobile terminal, and is attained by the operation of an insomnia treatment assistance program (hereinafter, referred to as an insomnia treatment application) stored in a storage medium such as RAM, ROM, a hard disk, or a semiconductor memory. Note that, the insomnia treatment application can also be installed by downloading the insomnia treatment application to the user terminal 100 through a network such as the internet.

The information input unit 11 inputs information indicating a bedtime, a fall-asleep time, a wakening time, and a get-up time of the user through a user manipulation with respect to an input interface (a touch panel, a keyboard, a mouse, and the like) of the user terminal 100. Such information input is performed every day. Note that, regarding the fall-asleep time, the user oneself is not capable of grasping the accurate time, and thus, an approximate time that is subjectively grasped may be input.

The information input by the information input unit 11 is stored in the sleep-related information storage unit 10 in association with a user ID. The user ID, for example, is identification information set for the insomnia treatment application when the insomnia treatment application is installed in the user terminal 100.

The sleep efficiency calculation unit 12 calculates a sleep efficiency of the user within a predetermined period, on the basis of the information indicating the bedtime, the fall-asleep time, the wakening time, and the get-up time of the user within the predetermined period, which is stored in the sleep-related information storage unit 10, and stores the result in the sleep-related information storage unit 10. The sleep efficiency refers to a percentage of time during which the user actually sleeps out of a total time during which the user stays in a bunk such as a bed. That is, the sleep efficiency is calculated using the following formula.

Sleep efficiency=(time from fall-asleep time to wakening time)/(time from bedtime to get-up time)×100[%]

Here, the predetermined period can be set in any manner, and in this embodiment, is 1 week as an example. For example, a period from a time after the get-up time on Sunday (may be other days of the week) as a commencement time to the same time after the get-up time on Sunday of the next week is set to the predetermined period. The commencement time of the predetermined period is set to any time after than a time when the user is assumed to be accurately awake.

In this case, the sleep efficiency calculation unit 12, for example, calculates the sleep efficiency of the user for 1 week, in accordance with the following expression.

Sleep efficiency=(total time from fall-asleep time to wakening time for 7 Days)/(total time from bedtime to get-up time for 7 Days)×100[%]

After the information indicating the bedtime, the fall-asleep time, the wakening time, and the get-up time is input by the information input unit 11 on the last day of the predetermined period, the sleep efficiency calculation unit 12, for example, calculates the sleep efficiency of the user for 1 week by the expression described above using the information for 7 days, which is stored in the sleep-related information storage unit 10.

As another method, each time when the information indicating the bedtime, the fall-asleep time, the wakening time, and the get-up time is input every day by the information input unit 11, the sleep efficiency calculation unit 12 may calculate the sleep efficiency of the day, may calculate the average value of the sleep efficiency for 7 days on the last day of the predetermined period, and may set the average value to the sleep efficiency for 1 week.

The bedtime setting unit 13 sets the bedtime of the user for each predetermined period, on the basis of the sleep efficiency calculated by the sleep efficiency calculation unit 12. When the bedtime is set, the bedtime setting unit 13 also uses a compliance status index value calculated by the compliance status index value calculation unit 14 (the details of a specific setting method will be described below).

The bedtime to be set by the bedtime setting unit 13 is a target bedtime to be followed by the user. Hereinafter, the target bedtime to be followed by the user will be referred to as a target bedtime. For example, the bedtime setting unit 13 sets the target bedtime in the predetermined period of the next week, on the basis of the sleep efficiency calculated by the sleep efficiency calculation unit 12 on the last day of the predetermined period, and similarly, the compliance status index value calculated by the compliance status index value calculation unit 14 on the last day of the predetermined period.

Figure 4:
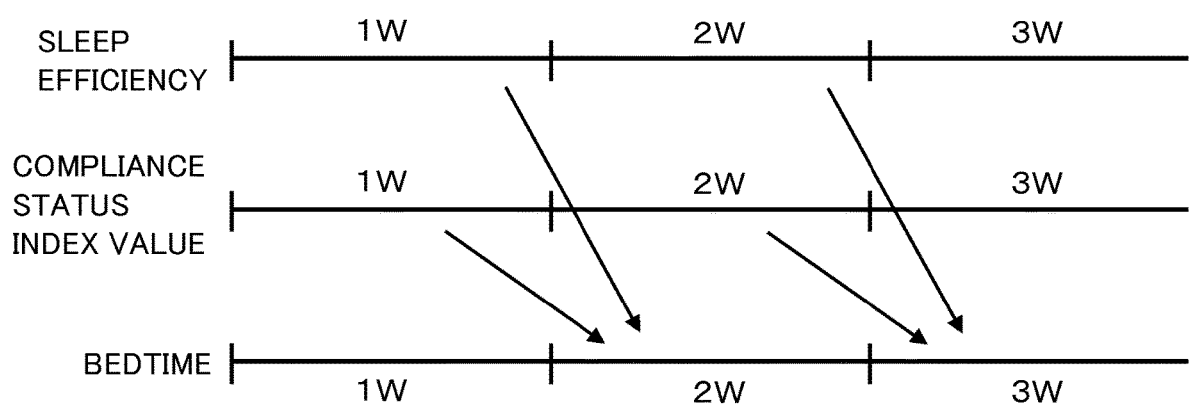
FIG. 4 is a diagram schematically illustrating an operation example of this embodiment.

That is, as illustrated in FIG. 4, the bedtime setting unit 13 sets the target bedtime of the second week, on the basis of the sleep efficiency of the first week, which is calculated by the sleep efficiency calculation unit 12, and the compliance status index value of the first week, which is calculated by the compliance status index value calculation unit 14. Similarly, the bedtime setting unit 13 sets the target bedtime of the third week, on the basis of the sleep efficiency of the second week, which is calculated by the sleep efficiency calculation unit 12, and the compliance status index value of the second week, which is calculated by the compliance status index value calculation unit 14. Note that, for the target bedtime of the first week, for example, a suitable time is set on the basis of an examination result of the medical institution.

The bedtime setting unit 13 notifies the set target bedtime of the next week to the user by displaying the set target bedtime on a display. In addition, the bedtime setting unit 13 stores the set target bedtime of the next week in the sleep-related information storage unit 10, and stores the target bedtime at least until the target bedtime is set again on the last day of the predetermined period of the next week. During the predetermined period of the next week, the user follows the notified target bedtime and tries to go to bed. By doing this every day, it is possible to expect that the quality of the sleep of the user is gradually improved.

The compliance status index value calculation unit 14 calculates the compliance status index value representing a status of whether the user complies with the target bedtime set by the bedtime setting unit 13 within the predetermined period. For example, the compliance status index value calculation unit 14 compares the actual bedtime that is input every day by the information input unit 11 with the target bedtime that is set by the bedtime setting unit 13 and stored in the sleep-related information storage unit 10, sets a day when the actual bedtime is later than the target bedtime to "compliance", sets a day when the actual bedtime is earlier than the target bedtime to "contravention", and calculates a compliance rate indicating a ratio of the days of "compliance" during the predetermined period as the compliance status index value. Alternatively, the number of days of "compliance" during the predetermined period may be calculated as the compliance status index value. Note that, even on the day when the actual bedtime is earlier than the target bedtime, a case where a time difference is within a predetermined time may be regarded as "compliance", as an error.

In this embodiment, in a case where the sleep efficiency calculated by the sleep efficiency calculation unit 12 is less than a first predetermined value (for example, 80%) and the compliance status index value calculated by the compliance status index value calculation unit 14 is a threshold value or more (for example, the compliance rate is 50% or more), the bedtime setting unit 13 sets a time that is a predetermined time (for example, 15 minutes) later than the previous set target bedtime as the next target bedtime (the bedtime to be followed by the user during the predetermined period of the next week).

In addition, in a case where the sleep efficiency calculated by the sleep efficiency calculation unit 12 is less than the first predetermined value and the compliance status index value calculated by the compliance status index value calculation unit 14 is less than the threshold value, the bedtime setting unit 13 sets a time that is identical to the previous set target bedtime as the next target bedtime.

Further, in a case where the sleep efficiency calculated by the sleep efficiency calculation unit 12 is a second predetermined value (for example, 85%) or more, the bedtime setting unit 13 sets a time that is predetermined time (for example, 15 minutes) earlier than the previous set target bedtime as the next target bedtime.

Note that, here, the first predetermined value (80%) used as the threshold value in the case of setting the target bedtime to be later than the previous set bedtime and the second predetermined value (85%) used as the threshold value in the case of setting the target bedtime to be earlier than the previous set bedtime are different values, and may be the same value. In addition, as a condition in the case of setting the target bedtime to be earlier than the previous set bedtime, an execution result of a sleepiness test may be used, in addition to the value of the sleep efficiency. For example, in a case where the sleep efficiency calculated by the sleep efficiency calculation unit 12 is the second predetermined value (for example, 85%) or more and the degree of sleepiness measured by the sleepiness test is further improved than the previous degree, a time earlier than the previous set target bedtime may be set as the next target bedtime.

The sleepiness test is test for measuring the degree of daytime sleepiness of the user. People suffering from insomnia do not sufficiently sleep on the night, and thus, often feel sleepiness during the day. The severity of the insomnia can be estimated in accordance with the degree of daytime sleepiness. In addition, by repeatedly implementing the sleepiness test, it is possible to estimate whether the insomnia is improved or worsen, or the degree of progress thereof.

The sleepiness test, for example, is a medical examination by interview using a known Epworth sleepiness scale (ESS), which is implemented by the function of the insomnia treatment application. ESS is a scale for subjectively grasping the daytime sleepiness with a medical interview sheet, and a score of 11 or more out of 24 is evaluated as having the daytime sleepiness.

Note that, the sleepiness test is not limited thereto. For example, predetermined display may be performed on the display of the user terminal 100 or a predetermined sound may be output from a speaker, and then, the elapsed time until the user performs a predetermined response manipulation is measured, and the degree of sleepiness (or the degree of awakening) may be determined on the basis of the elapsed time (the speed of response). In this case, it is determined that the degree of sleepiness increases as the response time increases.

The compliance status index value transmission unit 15 transmits the compliance status index value calculated by the compliance status index value calculation unit 14 to the server device 300, together with the user ID. The compliance status index value transmission unit 15 may perform the transmission when the compliance status index value is calculated by the compliance status index value calculation unit 14, or may perform the transmission at a predetermined timing after the compliance status index value is calculated.

Figure 3:
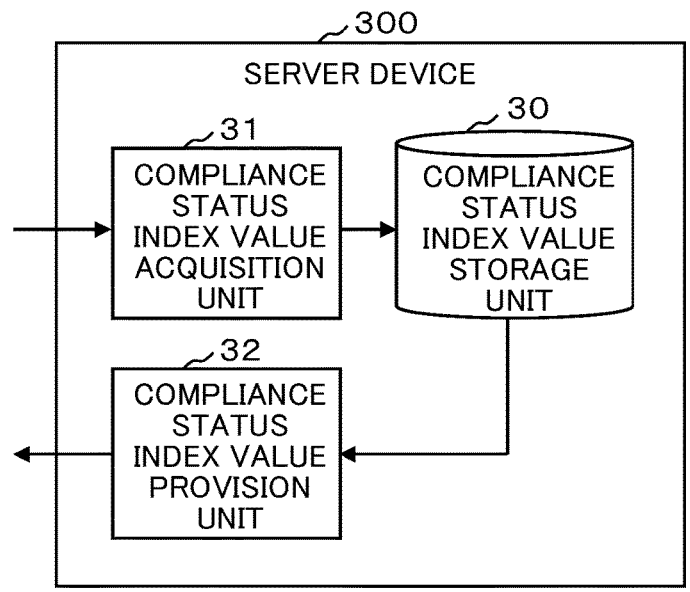
FIG. 3 is a block diagram illustrating a functional configuration example of a server device according to this embodiment.

FIG. 3 is a block diagram illustrating a functional configuration example of the server device 300 according to this embodiment. As illustrated in FIG. 3, the server device 300 of this embodiment includes a compliance status index value acquisition unit 31 and a compliance status index value provision unit 32, as a functional configuration. In addition, the server device 300 includes a compliance status index value storage unit 30, as a storage medium.

The compliance status index value acquisition unit 31 acquires the compliance status index value transmitted by the compliance status index value transmission unit 15 of the user terminal 100, and stores the compliance status index value in the compliance status index value storage unit 30, together with the user ID. The compliance status index value storage unit 30 sequentially stores the compliance status index value acquired for each predetermined period by the compliance status index value acquisition unit 31 for each user.

The compliance status index value provision unit 32 provides the compliance status index value stored in the compliance status index value storage unit 30 to the medical institution terminal 200, in accordance with a request from the medical institution terminal 200. For example, the medical institution terminal 200 accesses the server device 300, designates the user ID provided by the user, and requests the acquisition of the compliance status index value. In accordance with the request, the compliance status index value provision unit 32 generates a screen including the compliance status index value for each predetermined period, which is stored in the compliance status index value storage unit 30 in association with the user ID, as a list, and provides the screen to the medical institution terminal 200.

Accordingly, the compliance status index value for each predetermined period is shared between the user and the medical institution. In the medical institution, when the user visits the medical institution and receives the examination, it is possible to provide suitable advice on the basis of the compliance status index value for each predetermined period. In addition, by providing a mechanism of enabling bidirectional information exchange between the user terminal 100 and the medical institution terminal 200 through a web screen or the like provided by the server device 300, the advice may be provided to the user from the medical institution through the web screen.

Note that, here, a configuration has been described in which the compliance status index value is provided to the medical institution terminal 200 from the user terminal 100 through the server device 300, but information of the sleep efficiency may be further provided. In addition, information indicating everyday bedtime, fall-asleep time, wakening time, and get-up time, which is input by the information input unit 11, may be further provided.

In the embodiment described above, during the predetermined period, an example has been described in which the ratio or the number of days of "compliance" is calculated as the compliance status index value, but the invention is not limited thereto. For example, the compliance status index value calculation unit 14 may calculate the ratio or the number of days on which the user complies with the target bedtime in the second half period obtained by dividing the predetermined period into two periods, as the compliance status index value. For example, the ratio or the number of days on which the user complies with the target bedtime in the last 3 days of 1 week is calculated as the compliance status index value. As described above, when the target bedtime in the predetermined period of the next week is set on the last day of the predetermined period, the target bedtime can be set on the basis of the compliance status for the last 3 days.

In addition, in the embodiment described above, as illustrated in FIG. 4, an example has been described in which the target bedtime is set for each predetermined period (for each week), but the invention is not limited thereto. That is, an example has been described in which a period for calculating the sleep efficiency (and an interval for setting the target bedtime) and a period for calculating the compliance status index value are the same, but the invention is not limited thereto. For example, the period for calculating the sleep efficiency and the interval for setting the target bedtime may be shorter than the period for calculating the compliance status index value.

Figure 5:
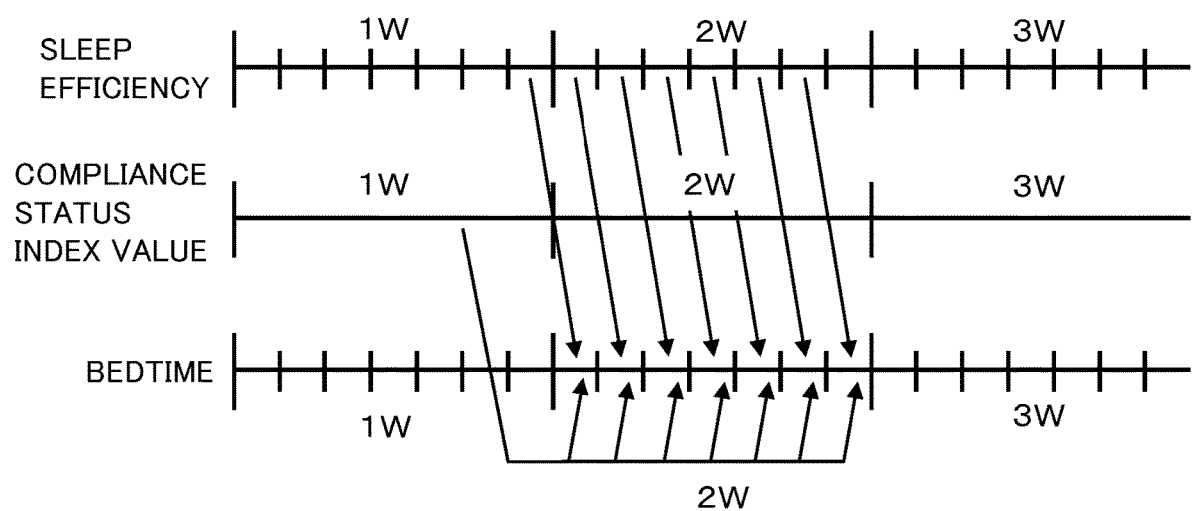
FIG. 5 is a diagram schematically illustrating another operation example of this embodiment.

For example, as illustrated in FIG. 5, the bedtime setting unit 13 may set the target bedtime (the target bedtime of the day on which the sleep efficiency is calculated after the get-up time) every day, on the basis of the sleep efficiency of the previous day that is calculated every day by the sleep efficiency calculation unit 12 after the get-up time is input by the information input unit 11, and the compliance status index value in the previous predetermined period (the previous week) that is calculated by the compliance status index value calculation unit 14. Note that, the compliance status index value is not calculated until the end of the first week, and thus, the target bedtime of the first week is set only on the basis of the sleep efficiency.

In this case, in a case where the sleep efficiency that is calculated by the sleep efficiency calculation unit 12 on a certain day within the predetermined period is less than the first predetermined value and the compliance status index value of the previous week that is calculated by the compliance status index value calculation unit 14 is the threshold value or more, the bedtime setting unit 13 sets a time that is a predetermined time later than the previous set target bedtime as the next target bedtime (the bedtime to be followed by the user on the night of the day on which the sleep efficiency is calculated).

In addition, in a case where the sleep efficiency that is calculated by the sleep efficiency calculation unit 12 on a certain day within the predetermined period is less than the first predetermined value and the compliance status index value of the previous week that is calculated by the compliance status index value calculation unit 14 is less than the threshold value, the bedtime setting unit 13 sets a time identical to the previous set target bedtime as the next target bedtime. Further, in a case where the sleep efficiency that is calculated by the sleep efficiency calculation unit 12 on a certain day within the predetermined period is the second predetermined value or more, the bedtime setting unit 13 sets a time that is a predetermined time earlier than the previous set target bedtime as the next target bedtime.

The bedtime setting unit 13 stores the currently set target bedtime in the sleep-related information storage unit 10, and stores the target bedtime at least until the target bedtime is set again on the next day. The compliance status index value calculation unit 14 compares the actual bedtime that is input every day by the information input unit 11 with the target bedtime that is set every day by the bedtime setting unit 13 and stored in the sleep-related information storage unit 10, and calculates the ratio or the number of days of "compliance" during the predetermined period as the compliance status index value.

In such a configuration, it is possible to flexibly adjust everyday target bedtime, on the basis of everyday sleep efficiency while avoiding the setting of the target bedtime that applies an excessive burden on the user, on the basis of the compliance status index value of the previous week.

In addition, the embodiment described above merely represents a specific example of implementing the invention, and the technical scope of the invention is not construed to be limited. That is, the invention can be implemented in various forms without departing from the gist or main characteristics thereof.

REFERENCE SIGNS LIST

10: sleep-related information storage unit
11: information input unit
12: sleep efficiency calculation unit
13: bedtime setting unit
14: compliance status index value calculation unit
15: compliance status index value transmission unit
30: compliance status index value storage unit
31: compliance status index value acquisition unit
32: compliance status index value provision unit
100: user terminal
200: medical institution terminal
300: server device

The invention claimed is:

1. An insomnia treatment assistance device comprising:
a sleep efficiency calculation unit calculating a sleep efficiency of a user, on the basis of information indicating a bedtime, a fall-asleep time, a wakening time, and a get-up time of the user;
a bedtime setting unit setting a target bedtime, on the basis of the sleep efficiency calculated by the sleep efficiency calculation unit, to notify the target bedtime to the user; and
a compliance status index value calculation unit calculating a compliance status index value representing a status of whether the user complies with the target bedtime set by the bedtime setting unit within a predetermined period,
wherein the bedtime setting unit sets a time later than a previous set bedtime as a next bedtime when the sleep efficiency calculated by the sleep efficiency calculation unit is less than a first predetermined value and the compliance status index value calculated by the compliance status index value calculation unit is a threshold value or more, sets a time identical to the previous set bedtime as the next bedtime when the sleep efficiency calculated by the sleep efficiency calculation unit is less than the first predetermined value and the compliance status index value calculated by the compliance status index value calculation unit is less than the threshold value, and sets a time earlier than the previous set bedtime as the next bedtime when the sleep efficiency calculated by the sleep efficiency calculation unit is a second predetermined value or more.

2. The insomnia treatment assistance device according to claim 1, wherein
the compliance status index value calculation unit calculates the compliance status index value representing a status of whether the user complies with the target bedtime in a second half period obtained by dividing the predetermined period into two periods.

3. The insomnia treatment assistance device according to claim 2, wherein
the sleep efficiency calculation unit calculates the sleep efficiency of the user within the predetermined period, on the basis of the information indicating the bedtime, the fall-asleep time, the wakening time, and the get-up time of the user within the predetermined period, and
the bedtime setting unit sets the target bedtime for each predetermined period, on the basis of the sleep efficiency calculated by the sleep efficiency calculation unit for each predetermined period.

4. The insomnia treatment assistance device according to claim 2, wherein
the sleep efficiency calculation unit calculates the sleep efficiency of the user within a period shorter than the predetermined period, on the basis of the information indicating the bedtime, the fall-asleep time, the wakening time, and the get-up time of the user within the period shorter than the predetermined period, and
the bedtime setting unit sets the target bedtime for each period shorter than the predetermined period, on the basis of the sleep efficiency calculated by the sleep efficiency calculation unit for each period shorter than the predetermined period.

5. The insomnia treatment assistance device according to claim 1, wherein
the sleep efficiency calculation unit calculates the sleep efficiency of the user within the predetermined period, on the basis of the information indicating the bedtime, the fall-asleep time, the wakening time, and the get-up time of the user within the predetermined period, and
the bedtime setting unit sets the target bedtime for each predetermined period, on the basis of the sleep efficiency calculated by the sleep efficiency calculation unit for each predetermined period.

6. The insomnia treatment assistance device according to claim 1, wherein
the sleep efficiency calculation unit calculates the sleep efficiency of the user within a period shorter than the predetermined period, on the basis of the information indicating the bedtime, the fall-asleep time, the wakening time, and the get-up time of the user within the period shorter than the predetermined period, and
the bedtime setting unit sets the target bedtime for each period shorter than the predetermined period, on the basis of the sleep efficiency calculated by the sleep efficiency calculation unit for each period shorter than the predetermined period.

7. An insomnia treatment assistance system comprising:
a user terminal used by a user;
a medical institution terminal used in a medical institution; and
a server device connected from the user terminal and the medical institution terminal,
wherein the user terminal includes:
a sleep efficiency calculation unit calculating a sleep efficiency of the user, on the basis of information indicating a bedtime, a fall-asleep time, a wakening time, and a get-up time of the user;
a bedtime setting unit setting a target bedtime, on the basis of the sleep efficiency calculated by the sleep efficiency calculation unit, to notify the target bedtime to the user;
a compliance status index value calculation unit calculating a compliance status index value representing a status of whether the user complies with the target bedtime set by the bedtime setting unit within a predetermined period; and
a compliance status index value transmission unit transmitting the compliance status index value calculated by the compliance status index value calculation unit to the server device,
the bedtime setting unit sets a time later than a previous set bedtime as a next bedtime when the sleep efficiency calculated by the sleep efficiency calculation unit is less than a first predetermined value and the compliance status index value calculated by the compliance status index value calculation unit is a threshold value or more, sets a time identical to the previous set bedtime as the next bedtime when the sleep efficiency calculated by the sleep efficiency calculation unit is less than the first predetermined value and the compliance status index value calculated by the compliance status index value calculation unit is less than the threshold value, and sets a time earlier than the previous set bedtime as the next bedtime when the sleep efficiency calculated by the sleep efficiency calculation unit is a second predetermined value or more, and
the server device includes:
a compliance status index value acquisition unit acquiring the compliance status index value transmitted by the compliance status index value transmission unit;
a compliance status index value storage unit storing the compliance status index value acquired by the compliance status index value acquisition unit for each user; and a compliance status index value provision unit providing the compliance status index value stored in the compliance status index value storage unit to the medical institution terminal, in accordance with a request from the medical institution terminal.

8. The insomnia treatment assistance system according to claim 7, wherein the compliance status index value calculation unit calculates the compliance status index value representing a status of whether the user complies with the target bedtime within a second half period obtained by dividing the predetermined period into two periods.

9. The insomnia treatment assistance system according to claim 8, wherein the compliance status index value provision unit further provides the sleep efficiency calculated by the sleep efficiency calculation unit, and the information indicating the bedtime, the fall-asleep time, the wakening time, and the get-up time, which is input by an information input unit, to the medical institution terminal, in addition to the compliance status index value.

10. The insomnia treatment assistance system according to claim 7, wherein the compliance status index value provision unit further provides the sleep efficiency calculated by the sleep efficiency calculation unit, and the information indicating the bedtime, the fall-asleep time, the wakening time, and the get-up time, which is input by an information input unit, to the medical institution terminal, in addition to the compliance status index value.

11. An insomnia treatment assistance program stored on a non-transitory computer readable medium comprising:

sleep efficiency calculation means for calculating a sleep efficiency of a user, on the basis of information indicating a bedtime, a fall-asleep time, a wakening time, and a get-up time of the user;

bedtime setting means for setting a target bedtime, on the basis of the sleep efficiency calculated by the sleep efficiency calculation means, to notify the target bedtime to the user; and compliance status index value calculation means for calculating a compliance status index value representing a status of whether the user complies with the target bedtime set by the bedtime setting means within a predetermined period, the program causing a computer to function as follows:

the bedtime setting means sets a time later than a previous set bedtime as a next bedtime when the sleep efficiency calculated by the sleep efficiency calculation means is less than a first predetermined value and the compliance status index value calculated by the compliance status index value calculation means is a threshold value or more, sets a time identical to the previous set bedtime as the next bedtime when the sleep efficiency calculated by the sleep efficiency calculation means is less than the first predetermined value and the compliance status index value calculated by the compliance status index value calculation means is less than the threshold value, and sets a time earlier than the previous set bedtime as the next bedtime when the sleep efficiency calculated by the sleep efficiency calculation means is a second predetermined value or more.

12. The insomnia treatment assistance program stored on a non-transitory computer readable medium according to claim 11, wherein the compliance status index value calculation means calculates the compliance status index value representing a status of whether the user complies with the target bedtime within a second half period obtained by dividing the predetermined period into two periods.

* * * * *